(12) United States Patent
Drake

(10) Patent No.: US 9,399,834 B1
(45) Date of Patent: Jul. 26, 2016

(54) ODOR REMOVAL ASSEMBLY

(71) Applicant: MoJack Distributors, LLC, Wichita, KS (US)

(72) Inventor: Daniel V. Drake, Wichita, KS (US)

(73) Assignee: MoJack Distributors, LLC, Wichita, KS (US)

( * ) Notice: Subject to any disclaimer, the term of this patent is extended or adjusted under 35 U.S.C. 154(b) by 0 days.

(21) Appl. No.: 14/662,032

(22) Filed: Mar. 18, 2015

(51) Int. Cl.
*D06M 11/34* (2006.01)
*C01B 13/10* (2006.01)
*A61L 2/20* (2006.01)
*A61L 2/24* (2006.01)

(52) U.S. Cl.
CPC ................ *D06M 11/34* (2013.01); *A61L 2/202* (2013.01); *A61L 2/24* (2013.01); *C01B 13/10* (2013.01); *A61L 2202/12* (2013.01); *A61L 2202/13* (2013.01); *A61L 2202/16* (2013.01)

(58) Field of Classification Search
CPC ........... A61L 2/20; A61L 2/202; A61L 2/208; A61L 2/24
See application file for complete search history.

(56) References Cited

U.S. PATENT DOCUMENTS

| | | | | |
|---|---|---|---|---|
| 5,588,529 | A | * | 12/1996 | Speck ......................... 206/315.1 |
| 5,681,533 | A | | 10/1997 | Hiromi |
| 5,845,780 | A | * | 12/1998 | Allen ............................ 206/579 |
| 6,134,806 | A | * | 10/2000 | Dhaemers ....................... 34/404 |
| 7,344,685 | B2 | | 3/2008 | McNulty |
| 7,582,257 | B2 | | 9/2009 | Bedard et al. |
| 7,939,015 | B1 | | 5/2011 | Elrod |
| 8,038,963 | B1 | | 10/2011 | Chen |
| 8,066,939 | B2 | | 11/2011 | Elrod |
| 8,187,533 | B2 | | 5/2012 | Elrod |
| 8,257,648 | B2 | | 9/2012 | Elrod |
| 8,329,096 | B2 | | 12/2012 | Elrod et al. |
| 8,367,010 | B2 | | 2/2013 | Chen |
| 8,388,900 | B2 | | 3/2013 | Benedek et al. |
| 8,404,180 | B1 | | 3/2013 | Elrod |

(Continued)

FOREIGN PATENT DOCUMENTS

| | | |
|---|---|---|
| CN | 202686785 | 1/2013 |
| WO | 9828974 A1 | 7/1998 |

OTHER PUBLICATIONS

OzoneLab, OzoneLab™ Insufflation Bags, Retrieved on Aug. 19, 2015 from Internet Site: http://www.ozoneservices.com/products/OLP/med/insufflation/ib.html, 4 pages total.

(Continued)

*Primary Examiner* — Timothy Cleveland
(74) *Attorney, Agent, or Firm* — Brient Globerman, LLC

(57) ABSTRACT

An odor removal assembly comprising a flexible bag that, when open, allows a user to place items into the bag's interior, and when closed, prevents a user from placing items into the interior of the bag. The bag may include a fastening mechanism for closing the bag. The assembly includes an ozone generator that generates ozone and expels the ozone through a conduit that extends between an outlet of the ozone generator and the interior of the bag. The assembly may also include an ozone destruction catalyst for removing ozone from the interior of the bag. In various embodiments, the odor removal assembly includes an automatic shutoff system for preventing the ozone generator from generating ozone gas if: the ozone level exceeds a pre-determined level outside of the bag, if the ozone level exceeds a pre-determined level within the interior of the bag, and/or if the bag is open.

12 Claims, 7 Drawing Sheets

(56) References Cited

U.S. PATENT DOCUMENTS

| | | |
|---|---|---|
| 8,557,177 B1 | 10/2013 | Elrod |
| 2003/0044308 A1 | 3/2003 | Toth |
| 2004/0028572 A1 | 2/2004 | Sham et al. |
| 2004/0222165 A1 | 11/2004 | Michocki et al. |
| 2004/0231696 A1* | 11/2004 | Wen .................................. 134/1 |
| 2008/0118411 A1 | 5/2008 | D'Arinzo |
| 2010/0047119 A1 | 2/2010 | Cressy |
| 2010/0289655 A1 | 11/2010 | Elrod et al. |
| 2011/0110820 A1 | 5/2011 | Mann |
| 2011/0268625 A1* | 11/2011 | Chen ............................ 422/294 |
| 2011/0293484 A1 | 12/2011 | Stausgaard et al. |

OTHER PUBLICATIONS

Jenesco, Hunters—spread the word! (instead of your smell), Retrieved on Aug. 19, 2015 from Internet Site http://www.jenesco.com/hunter-scent-removerhtml, 4 pages total.

* cited by examiner

ODOR REMOVAL ASSEMBLY

BACKGROUND

Removing odors from items such as clothing and other gear has become increasingly important to hunters, sportsmen, and to the general public. Accordingly, there is a need for improved devices that make removing odors from these items more efficient. There is currently a particular need for removing odors from athletic gear such as athletic jerseys, pads, helmets, braces, shoes, athletic gear, and hunting gear. Various embodiments of the present odor removing ozone assembly recognize and address the foregoing considerations, and others, of prior art devices.

SUMMARY

An assembly for removing odors from clothing or other items, according to various embodiments, includes a flexible bag, or other suitable container, that defines an interior and a closeable opening that is dimensioned so that when the opening is in an open orientation, a user may place clothing and/or one or more other objects, into the interior of the bag through the opening. The flexible bag and the closeable opening are dimensioned so that when the opening is in a closed orientation, a user is prevented from placing clothing or one or more other objects into the interior of the bag through the opening. In various embodiments, the assembly has a fastening mechanism for selectively maintaining the bag in the closed orientation. The assembly may also include an ozone generator that is adapted to generate ozone gas and to expel the ozone gas from the ozone generator through an outlet. The assembly may also include at least one conduit that extends in gaseous communication between the outlet of the ozone generator to the interior of the flexible bag. The assembly may further include an ozone destruction catalyst disposed within an interior portion of the flexible bag. In further embodiments, the assembly includes an automatic shutoff system that is adapted to prevent the operation of the ozone generator at least partially in response to one or more pre-determined conditions being satisfied (e.g., the ozone level inside or outside of the flexible bag's interior being above a predetermined level).

BRIEF DESCRIPTION OF THE DRAWINGS

Various embodiments of an assembly for removing odors from clothing or other items are described below. In the course of this description, reference will be made to the accompanying drawings, which are not necessarily drawn to scale and wherein.

DETAILED DESCRIPTION

Various embodiments will now be described more fully hereinafter with reference to the accompanying drawings. It should be understood that the invention may be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Structure of Odor Removal Assembly

Figure 1:
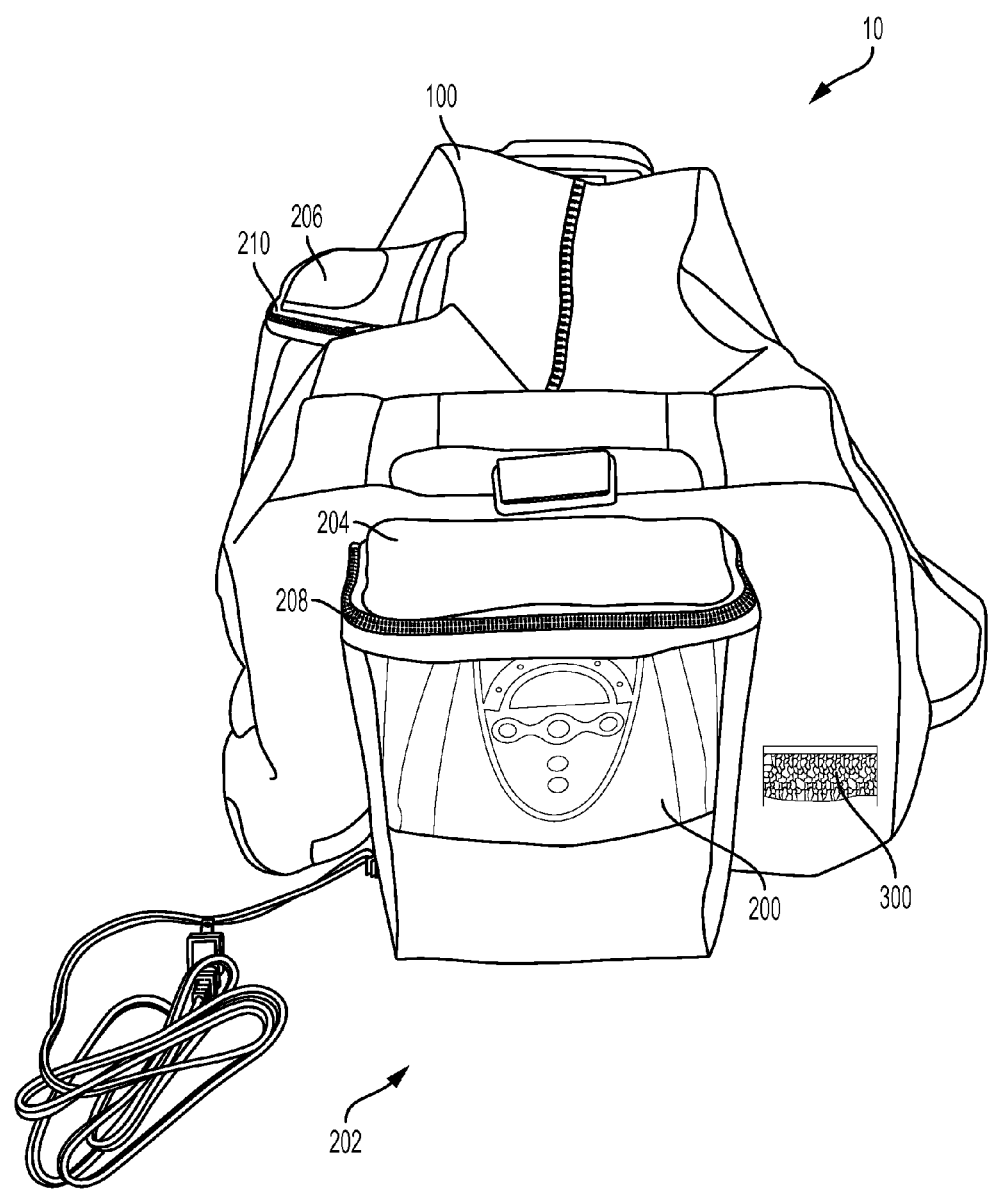
FIG. 1 is an end perspective view of an embodiment of an assembly for removing odors, in a closed orientation.

As shown in FIG. 1, an odor removal assembly 10, according to various embodiments, includes: (1) a flexible bag 100; (2) an ozone generator 200; and (3) an ozone destruction catalyst 300. These various components are discussed in more detail below.

Flexible Bag

Figure 2:
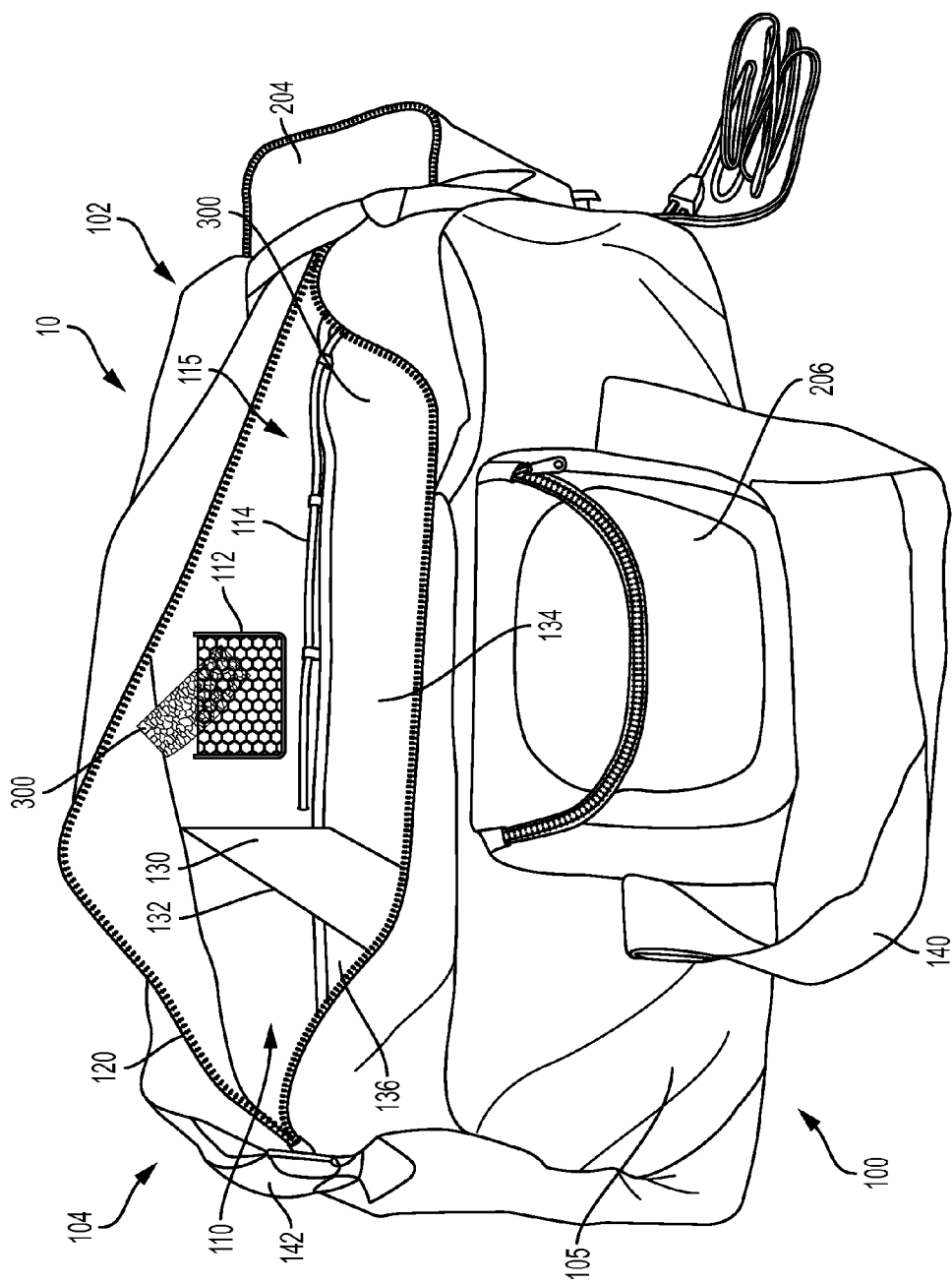
FIG. 2 is a side perspective view of the assembly of FIG. 1, in an open orientation.

Referring to FIG. 2, the odor removal assembly 10, in various embodiments, includes a flexible bag 100 (or other flexible or non-flexible container) that is configured for storing clothing and/or other items within its interior. In various embodiments, the flexible bag 100 may be a flexible container such as a portable closet. For example, the portable closet may have a removable clothing rod for hanging athletic apparel and may have foldable shelving for holding other athletic gear. In other embodiments, the flexible bag 100 may be a non-flexible container such as a steel closet. In various embodiments, the steel closet may be any suitable size (e.g., 2-10 feet tall, 2-10 feet wide, 2-10 feet deep, etc.). The flexible bag 100 may be any suitable size or shape (e.g., cubical, cylindrical, spherical, conical, hexagonal, etc.). In some embodiments, the flexible bag 100 may include ribbing, piping, or any other suitable structural material to maintain the shape of the flexible bag 100. The flexible bag 100 may be made of fabric or any other suitable flexible material (e.g., fabric, ballistic nylon, plastic, etc.). In various embodiments, the flexible bag 100 may be made of non-flexible material. In particular embodiments, the flexible bag 100 may be made of water-resistant material (e.g., GORE-TEX®). In other embodiments, the flexible bag 100 may be made at least partially from an activated carbon material.

In the embodiment shown in FIGS. 1-7, the flexible bag 100 includes a central housing 105 that defines an interior portion 110. The central housing 105 defines a first end 102 and a second end 104 and an opening 115 intermediate the housing's first and second ends 102, 104 through which a user may selectively access the interior portion 110 of the central housing. In particular embodiments, the opening 115 may be in any suitable shape. In various embodiments, the opening 115 may be parallel to a central axis that extends between the first and second ends 102, 104 of the central housing 105. In other embodiments, the opening 115 may be substantially perpendicular to the central axis that extends between the first and second ends 102, 104 of the central housing 105. In still other embodiments, the opening 115 may be substantially U-shaped.

In various embodiments, when the flexible bag opening 115 is in an open orientation, as shown in FIG. 2, a user may place clothing, or one or more other objects, into the interior portion 110 of the central housing 105 through the opening 115. In particular embodiments, when the opening 115 is in a closed orientation, as shown in FIG. 1, a user is prevented from placing clothing, or other objects, into the interior portion 110 of the central housing 105 though the opening 115.

As shown in FIGS. 1 and 2, the flexible bag 100 may include a fastening mechanism 120 for selectively maintaining the bag opening 115 in a closed orientation. The fastening mechanism 120 may comprise any suitable fastening mechanism (e.g., a zipper; one or more buttons; a hinged door; a hook and loop fastening assembly; a ziplock arrangement, etc.). In particular embodiments, the fastening mechanism 120 may comprise a zipper. In various embodiments, the opening 115 and the fastening mechanism 120 are the same length. For example, where the opening 115 is parallel to the axis that extends between the first and second ends 102, 104 of the central housing 105, the fastening mechanism 120 is also parallel to this axis. In some embodiments, the fastening mechanism 120 may extend the entire length of the central housing 105 from the housing's first end 102 to the housing's second end 104. In other embodiments, the fastening mechanism 120 may cover only a portion of the length intermediate the housing's first and second ends 102, 104. In various embodiments, the fastening mechanism 120 may also include a locking mechanism (not shown). The locking mechanism may be any suitable locking mechanism (e.g., a padlock, a combination lock, etc.). The locking mechanism may be used to prevent unwanted access by children and/or others into the interior portion 110 of the bag 100 by maintaining the fastening mechanism 120 in the closed orientation.

Referring again to FIG. 2, in various embodiments, the interior portion 110 of the central housing 105 may be dimensioned to hold athletic apparel, sporting goods, shoes, and/or any other gear and/or apparel. In some embodiments, the interior portion 110 of the central housing 105 may be coated (e.g., partially or entirely) with an ozone destruction material. In other embodiments, the interior portion 110 of the central housing 105 may include one or more interior pockets 112. In various embodiments, the one or more interior pockets 112 may be made of any suitable flexible material, such as a mesh material.

In some embodiments, the one or more interior pockets 112 may be integrally formed with an interior surface of the central housing. In other embodiments, the one or more interior pockets 112 may be selectively detachable from the central housing's interior surface. In certain embodiments, the one or more interior pockets 112 may include a fastening mechanism (not shown) (e.g., a zipper, one or more buttons, a hook and loop fastening assembly, etc.) for selectively maintaining an opening of one or more of the interior pockets 112 in a closed position to retain items within the interior pockets 112.

In particular embodiments, the one or more interior pockets 112 are configured to hold ozone destruction material such as the ozone destruction catalyst 300. In various embodiments, the one or more interior pockets 112 serve as an ozone destruction catalyst support assembly that is adapted for supporting the ozone destruction catalyst 300 within the interior portion 110 of the flexible bag's central housing 105. In particular embodiments, the ozone destruction catalyst support assembly comprises at least one mesh pocket.

In various embodiments, a partition 130 may be located within the central housing's interior portion 110. The partition 130 may be made of any suitable (e.g., sturdy) material (e.g., foam, cardboard, plastic, etc.). In various embodiments, the partition 130 is made of foam and covered with the same material that the interior of the flexible bag 100 is made of. In some embodiments, the partition 130 may be selectively detachable from the central housing's interior portion 110. For example, an outer circumferential edge 132 of the partition 130 may include hook fastening material that is attachable to loop fastening material running the length of the interior portion 110 of the central housing 105 from the central housing's first end 102 to the central housing's second end 104. In certain embodiments, the size and shape of the partition 130 may correspond to the size and shape of a cross section of the central housing's interior portion 110 such that, when the partition 130 is inserted into the interior portion 110, the partition 130: (1) engages one or more interior walls of the flexible bag 100 and is held in place by friction; and (2) divides the interior portion 110 of the central housing 105 into two separate interior chambers 134, 136.

In particular embodiments, the partition 130 may be adapted to be moved between: (1) a first position, in which the partition 130 cooperates with one or more interior walls of the bag's central housing 105 to form a first interior chamber 134 of a first size; and (2) a second position, in which the partition 130 cooperates with the one or more interior walls of the flexible bag 100 to form a first interior chamber 134 (on the same side of the partition 130) that is of a second size that is different from the first size. In some embodiments, the second size of the first interior chamber 134 is larger than the first size of the first interior chamber 134. In particular embodiments, when: (1) the partition 130 is in the first position, a conduit 114 extends in gaseous communication between an outlet of the ozone generator 222 and the first interior chamber 134; and (2) the partition 130 is in the second position, the conduit 114 extends in gaseous communication between an outlet of the ozone generator 222 and the second interior chamber 136.

Returning to FIG. 1, an exterior portion 202 of the flexible bag 100 may include one or more exterior pockets 204, 206. In various embodiments, the one or more exterior pockets 204, 206 may be made of any suitable material (e.g., flexible material). In particular embodiments, the one or more exterior pockets 204, 206 may be made of mesh material. In other embodiments, the one or more exterior pockets 204, 206 may be made of transparent material such as plastic. In some embodiments, the one or more exterior pockets 204, 206 may be integrally formed with the flexible bag's exterior portion 202. In other embodiments, the one or more exterior pockets 204, 206 may be detachable from the flexible bag exterior portion 202. In yet other embodiments, the one or more exterior pockets 204, 206 may include a fastening mechanism 208, 210 (e.g., zipper, one or more buttons, hook and loop fastening assembly, etc.) for keeping contents within the one or more exterior pockets 204, 206. In particular embodiments, a particular exterior pocket 204 is configured to hold the ozone generator 200. In various embodiments, the exterior pocket 204 is an ozone generator support assembly that is adapted for supporting the ozone generator 200 within the interior portion of the exterior pocket 204.

Figure 3:
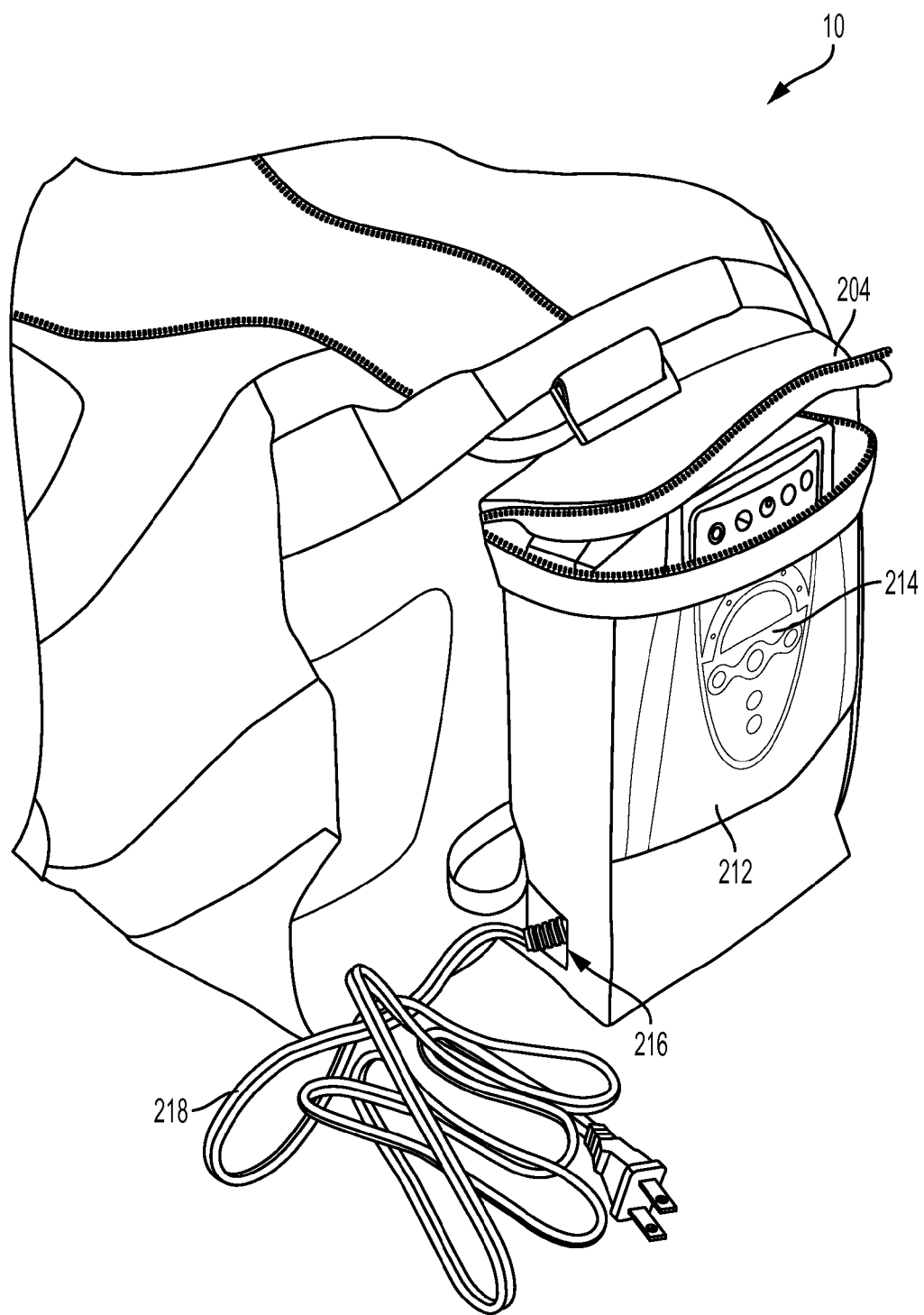
FIG. 3 is a partial end perspective view of the assembly of FIG. 1 showing an ozone generator located inside an exterior pocket of the assembly.
Figure 4:
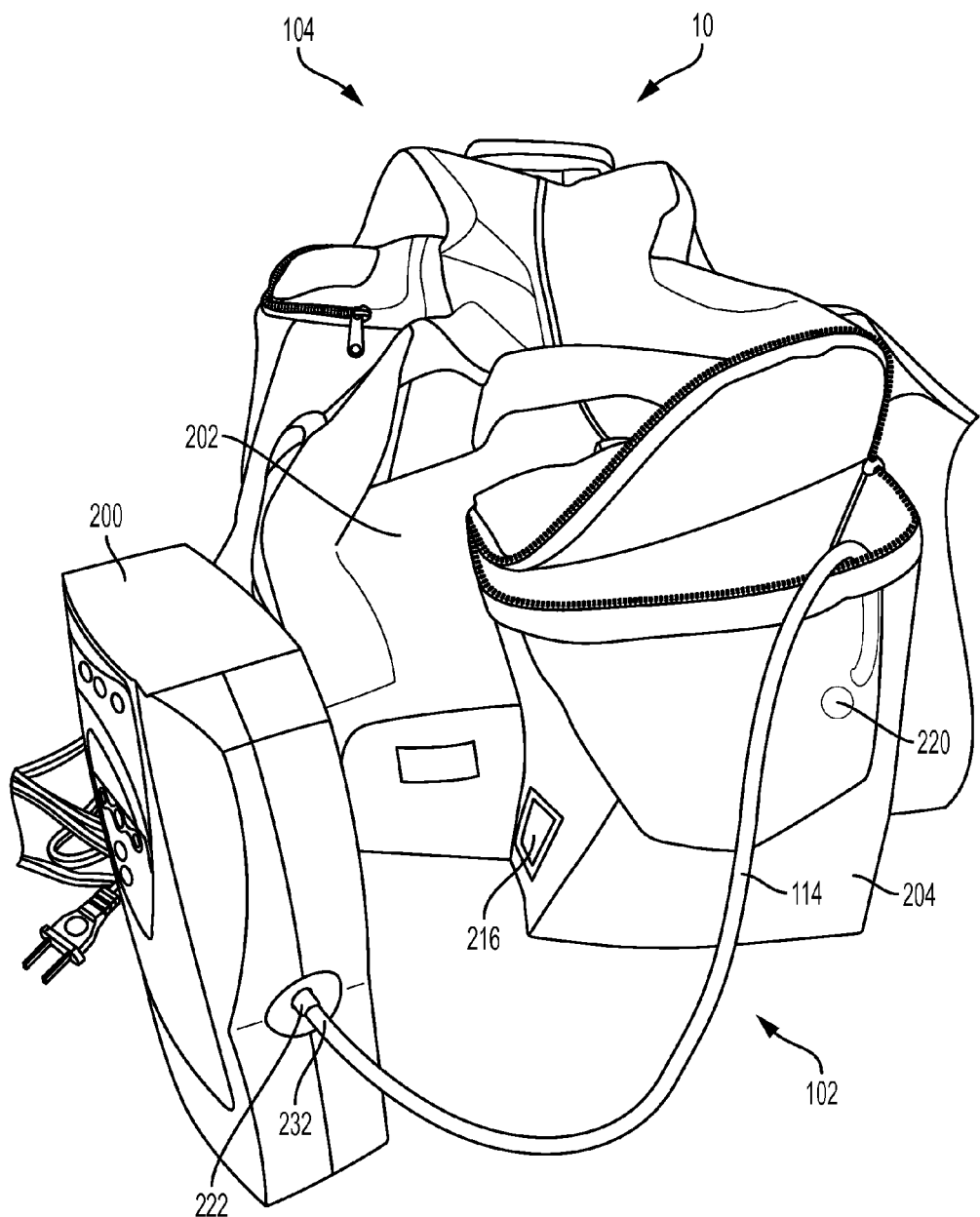
FIG. 4 is an end perspective view of the assembly of FIG. 1, showing an ozone generator located outside of the assembly with a conduit for ozone attached to the ozone generator.

Referring to FIGS. 3 and 4, the exterior pocket 204 is shown in an open orientation. In various embodiments, the exterior pocket 204 has a transparent front portion 212 for viewing the contents of the pocket. For example, when the ozone generator is located within the interior of the exterior pocket 204, a user may view a user interface 214 of the ozone generator 200. In particular embodiments, the exterior pocket 204 has a first opening 216 for allowing a power cord 218 associated with the ozone generator 200 to pass through to the outside of the flexible bag 100. Referring specifically to FIG. 4, in various embodiments, the exterior pocket 204 has a second opening 220 for allowing the conduit 114 to pass through from the ozone generator 200 to the interior portion 110 of the bag 100 so that the conduit 114 extends in gaseous communication between the outlet 222 of the ozone generator 200 to the interior portion 110 of the bag 100.

Referring again to FIG. 2, the flexible bag 100 has one or more straps 140 and one or more handles 142 connected to the flexible bag's exterior portion 202 for carrying and handling of the flexible bag 100. The one or more straps 140 and the one or more handles 142 may be made of any sturdy, flexible material (e.g., woven nylon). In various embodiments, the one or more straps 140 and the one or more handles 142 may be integrally formed with the flexible bag 100. In other embodiments, the one or more straps 140 and the one or more handles 142 may be connected to the exterior portion of the bag 202 in any suitable way. For example, the one or more straps 140 and the one or more handles 142 may be sewn into the exterior portion of the bag 202.

Ozone Generator

Figure 5:
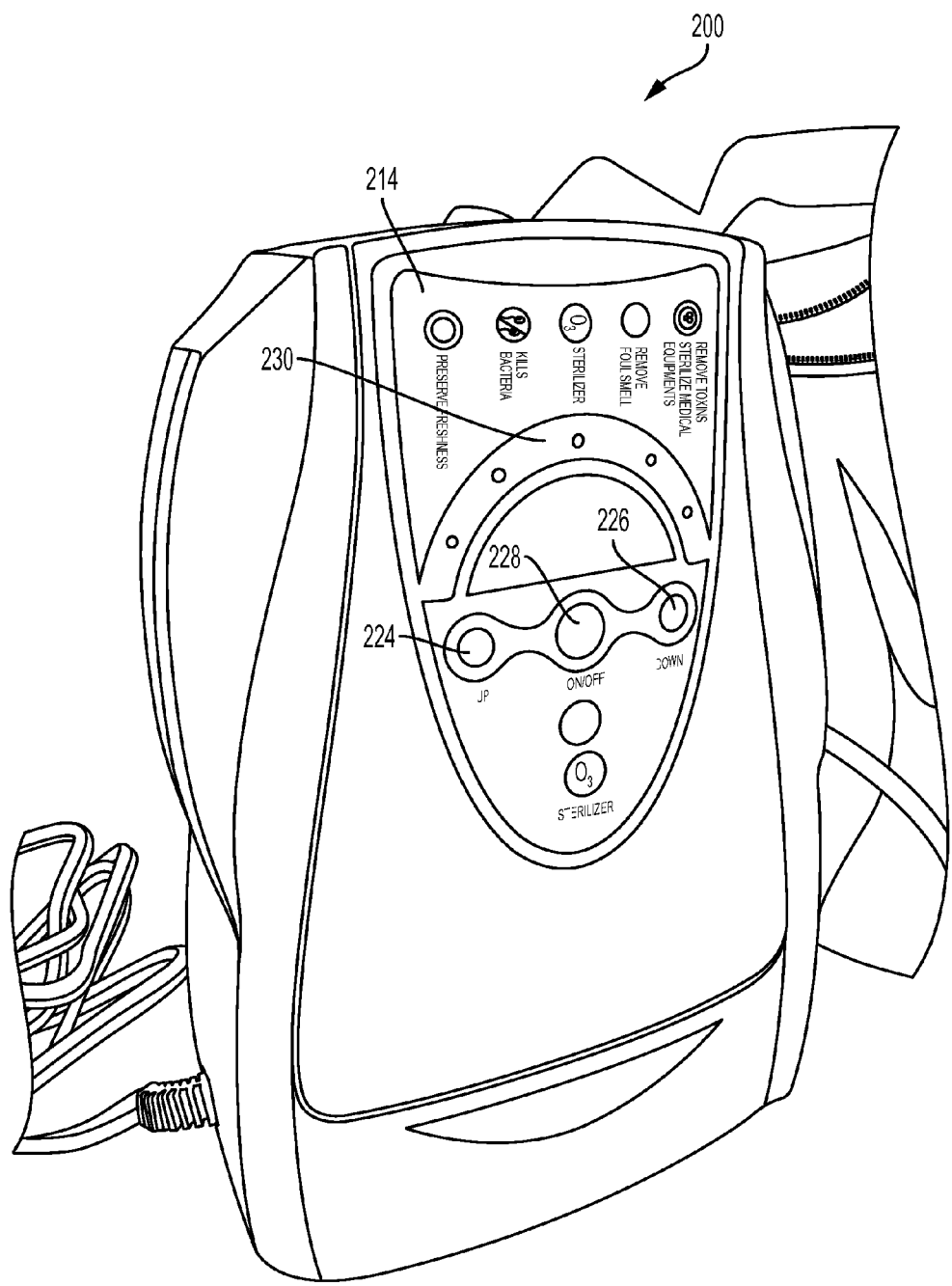
FIG. 5 is a front perspective view of the ozone generator.

Referring to FIGS. 4 and 5, in various embodiments, the odor removal assembly 10 includes any suitable ozone generator 200 (e.g., an electric ozone generation device) configured to generate ozone. In various embodiments, the ozone generator 200 may be positioned in any suitable location adjacent the flexible bag 100. In particular embodiments, the ozone generator 200 may be disposed adjacent the exterior portion of the bag 100. In other embodiments, the ozone generator 200 may be positioned within one of the one or more exterior pockets 204, 206. In some embodiments, the ozone generator 200 may be positioned so that it is spaced apart from the flexible bag 100. In particular embodiments, the ozone generator 200 may be operatively coupled to the flexible bag 100.

In various embodiments, the ozone generator 200 generates ozone and expels it through the outlet 222, as shown in FIG. 4. The ozone generator 200 may, for example, generate ozone in a concentration that is suitable for removing odors from clothing and other items. In particular embodiments, the ozone generator 200 includes power cord 218 operatively coupled to the ozone generator 200. In some embodiments, the power cord 218 comprises a standard wall plug. In other embodiments, the power cord 218 comprises a 12-volt car plug, or other suitable plug.

In various embodiments, the ozone generator 200 includes a user interface 214 and a computer processor (not shown) for allowing a user to regulate the amount of ozone that the ozone generator 200 generates in a particular deodorizing session. In particular embodiments, the user interface 214 may include control buttons 224, 226 for adjusting the level of ozone expelled from the ozone generator 200 up or down, respectively. In various embodiments, the user interface 214 may also include a power button 228 for turning the ozone generator on or off.

In particular embodiments, the ozone generator 200 may include a timer 230 with a display on the user interface 214 for allowing a user to select the amount of time that the ozone generator will operate in a particular session. In various embodiments, the timer 230 may allow a user to select a specific period of time (e.g., seconds, minutes, hours, etc.). In other embodiments, the timer 230 may allow a user to select a pre-set time limit (e.g., five minutes, 10 minutes, 15 minutes, 30 minutes, one hour, etc.). In some embodiments, the timer 230 may use a suitable selectable program for setting the timer (e.g., "preserve freshness", "kill bacteria", "sterilize", "remove foul smell", and "remove toxins/sterilize medical equipment"). For example, in a particular embodiment, the ozone generator may be adapted to run for five minutes in response to a user selecting a "preserving freshness" button. As a further example, for items that require a significant amount of deodorizing, a user may select a program that is longer in duration.

In various embodiments, the ozone generator 200 may include, or otherwise be coupled to, an ozone sensor (not shown), which may be adapted to communicate with a controller within the ozone sensor via a suitable communications channel (e.g., a suitable wired or wireless communications channel). The ozone sensor may be adapted for sensing the concentration of ozone adjacent the sensor. In particular embodiments, the controller may be adapted to prevent the operation of the ozone generator (e.g., turn off the ozone generator, or prevent the ozone generator from being turned on) at least partially in response to (e.g., in response to) the ozone sensor sensing one or more predetermined ozone levels (e.g., ozone concentration levels) adjacent the ozone sensor.

In some embodiments, the ozone sensor may be positioned at any suitable location [e.g., inside the flexible bag 100 (e.g., within the interior portion 110 of the central housing 105), or outside of the flexible bag 100 (e.g., adjacent the ozone generator 200)]. As noted above, in various embodiments, the ozone generator's controller may be adapted to turn off or otherwise modify the ozone generator's output of ozone in response to the ozone concentration measured by the ozone sensor reading an ozone concentration level above a pre-determined threshold, and thereby satisfying a pre-determined condition. For example, the ozone generator 200 may be adapted to turn off for safety reasons and/or to prevent potential damage to clothing or other items within the flexible bag 100 caused by over-exposure to excessively high levels of ozone. In some embodiments, the controller may turn off the ozone generator 200 in response to the ozone sensor sensing an ozone level above a particular pre-determined threshold outside of the flexible bag 100. In other embodiments, the controller may turn off the ozone generator 200 in response to the ozone sensor sensing an ozone level above a particular pre-determined threshold outside of the flexible bag 100 within an interior portion of the flexible bag 100 (e.g., within the central housing's interior 110).

In particular embodiments, the ozone generator's controller may be adapted to turn off the ozone generator 200 at least partially in response to (e.g., in response to) the ozone sensor and/or the controller sensing that the flexible bag 100 (e.g., the central housing 105) has been opened (or is otherwise in an open position). In particular embodiments, the controller (which may be computerized) may, for example, be programmed to assume that the central housing 105 has been opened in response to detecting a relatively sudden drop in ozone concentration within the bag (e.g., a concentration drop above a predetermined threshold within a predetermined period of time).

Similarly, the controller may be programmed to assume that the central housing 105 is open based, at least in part, on: (1) the length of time that the ozone generator has been running; and (2) the change in ozone concentration within the interior of the bag (e.g., central housing 105) over time. For example, the controller may be programmed to assume that the bag (e.g., the bag's central housing 105) is in an open orientation if the ozone concentration level within the bag's interior (e.g., within the interior portion 110 of the central housing 105) doesn't reach a pre-determined threshold level in response to the ozone generator running for a pre-determined period of time.

In other embodiments, the ozone generator 200 may include any other suitable type of sensor for sensing whether the bag 100 is in an open or closed orientation (e.g., a suitable mechanical sensor or other sensor). In such embodiments, the controller may be adapted to prevent operation of the ozone generator in response to this sensor sensing that the bag 100 is in an open orientation.

Figure 6:
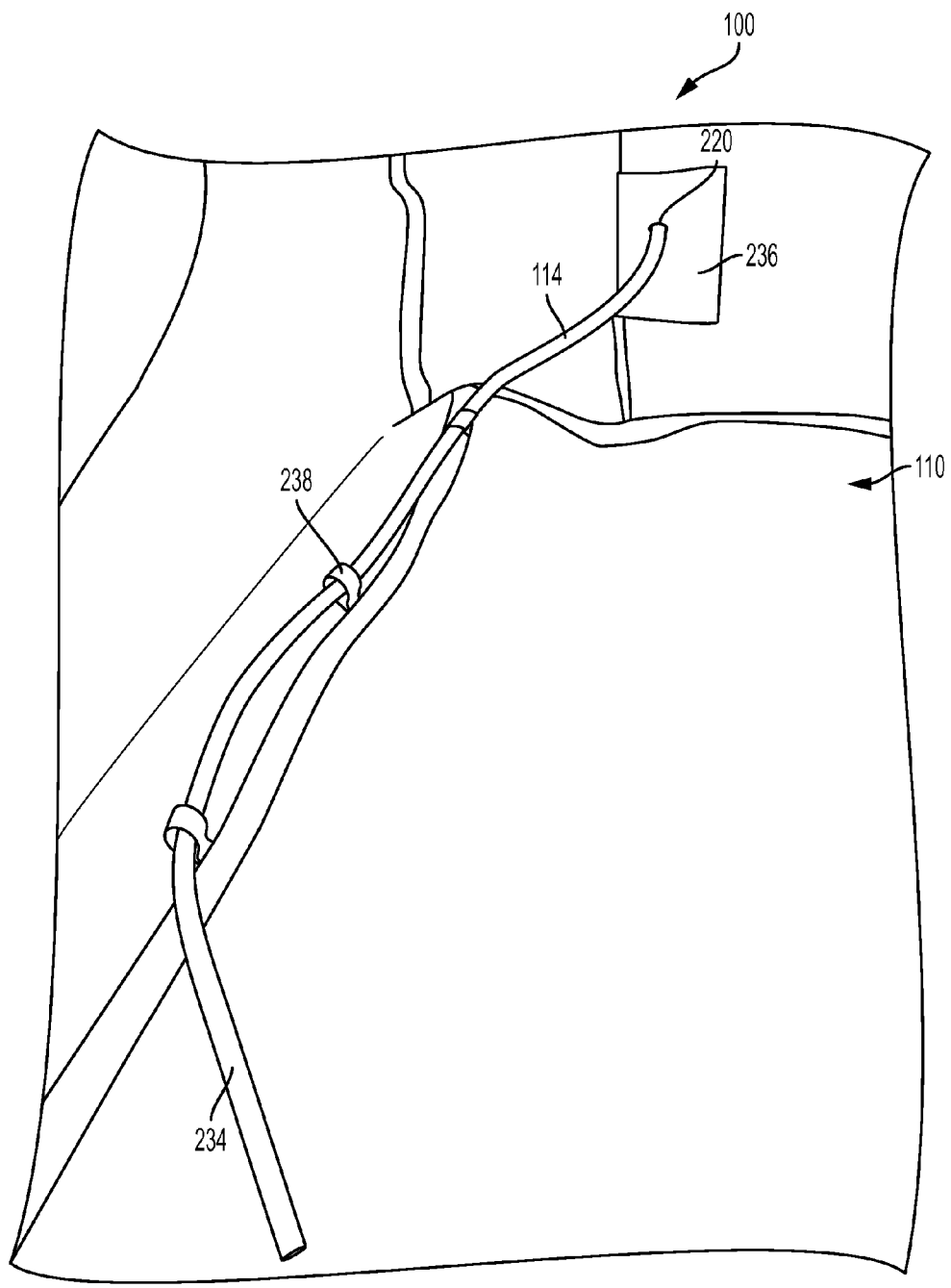
FIG. 6 is a partial perspective view of an inside surface of the assembly of FIG. 1.

Conduit for Transferring Ozone from the Ozone Generator to the Interior of the Flexible Bag Referring to FIGS. 4 and 6, in various embodiments, the odor removal assembly 10 includes a conduit 114 that is disposed at least partially within the interior portion of the bag 100. The conduit 114 is in gaseous communication between the outlet of the ozone generator 222 and the interior portion of the flexible bag 100 for transferring ozone from the ozone generator 200 to the interior portion of the bag 100. In particular embodiments, the conduit 114 is adapted to facilitate the flow of ozone from the ozone generator outlet 222 into the interior portion of the flexible bag 100. Referring specifically to FIG. 4, in particular embodiments, the conduit 114 has a first end 232 operatively coupled to the ozone generator 200. Referring specifically to FIG. 6, according to various embodiments, the conduit 114 has a second end 234 disposed within the interior portion of the bag 100. In various embodiments, the conduit second end 234 may be positioned in any suitable location within the interior portion of the bag 100. For example, the conduit second end 234 may be in a central portion of the interior portion of the bag (e.g., substantially midway between the flexible bag's first and second ends 102, 104). In some embodiments, the conduit 114 may extend through the pocket second opening 220 such that the conduit 114 extends between the exterior pocket 204 and the interior portion of the bag 100. In particular embodiments, the second opening 220 may be surrounded by backing 236 to preserve the size and shape of the second opening 220.

In various embodiments, the conduit 114 may be tubing or any other suitable conduit. In particular embodiments, the conduit is made of flexible material. In other embodiments, the conduit is made of non-flexible material. In various embodiments, the conduit 114 may be elongated and relatively long (e.g., 1-15 feet in length). In some embodiments, the conduit 114 may be integrally formed with the interior portion of the bag 100. In other embodiments, the interior portion of the bag 100 may include one or more straps 238 or other fastening arrangements for holding the conduit 114 in place. The one or more straps 238 may be made from any suitable sturdy material (e.g., woven nylon, etc.). In various embodiments, the one or more straps 238 may be connected to the interior portion of the bag 100 in any suitable way. For example, the one or more straps 238 may be sewn into the interior portion of the bag 100.

Ozone Destruction Catalyst

Figure 7:
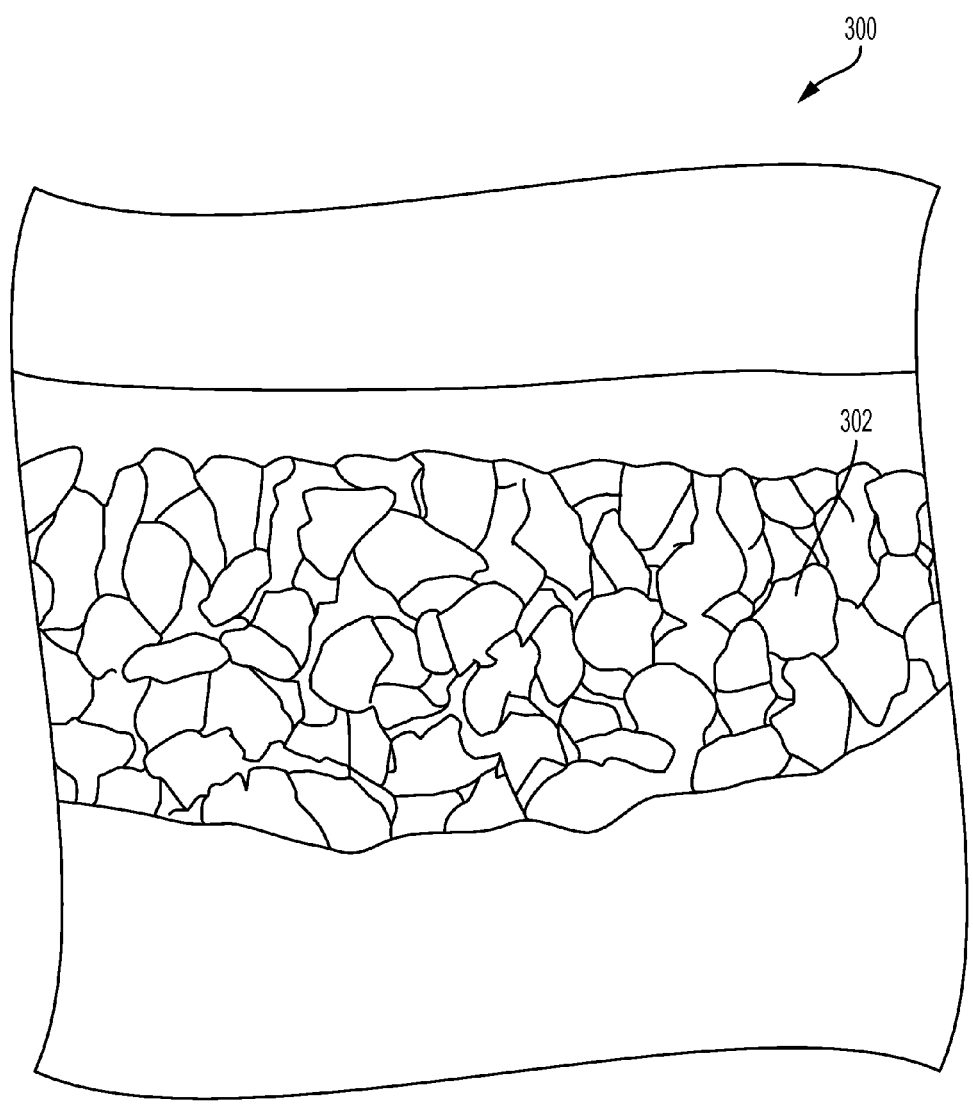
FIG. 7 is a front view of an ozone destruction catalyst for use within the assembly of FIG. 1.

Referring to FIG. 7, the odor removal assembly 10, according to various embodiments, includes an ozone destruction catalyst 300. In particular embodiments, the ozone destruction catalyst 300 may comprise any suitable catalyst 302 for destroying ozone (e.g., CuO and $MnO_2$, Au, Pd, Pt, etc.). The ozone destruction catalyst 300 may, in various embodiments, catalyze ozone ($O_3$) into oxygen ($O_2$) through a catalytic reaction. The ozone destruction catalyst 300 may be used, for example, to prevent damage to clothing or other items within the bag and/or to prevent over-exposure to ozone by humans and other living organisms outside of the bag 100 caused by excessively high levels of ozone.

As previously discussed, the one or more interior pockets 112 may be configured to hold the ozone destruction catalyst 300 such that the ozone destruction catalyst 300 is disposed and maintained within the interior portion of the flexible bag 100. In various embodiments, the ozone destruction catalyst 300 may be in any suitable form (e.g., in the form of one or more spheres, cylinders, honeycombs etc.). In some embodiments, the ozone destruction catalyst 300 is a pellet catalyst. In particular embodiments, the ozone destruction catalyst 300 and/or the flexible bag 100 are configured so that the ozone destruction catalyst 300 may be selectively removed from the interior portion 110 of the flexible bag 100. In such embodiments, if the ozone destruction catalyst 300 needs to be replaced, a user may remove the ozone destruction catalyst 300 (e.g., from the interior pocket 112) and replace it with new ozone destruction catalyst.

Assembling the Ozone Removal Assembly

Referring generally to FIGS. 1-6, and especially FIG. 4, the odor removal assembly 10 may be assembled by placing the conduit 114 into the exterior pocket 204 and then through the exterior pocket second opening 220 that provides a gateway into the interior portion 110 of the bag's central housing 105. Once the conduit 114 is positioned so that it extends through the second opening 220, the conduit 114 may then be passed through the one or more straps 238 located in the interior portion of the flexible bag 100. After moving the conduit 114 into place, the ozone generator's power cord 218 may be pulled through the exterior pocket's first opening 216 and the ozone generator 200 may then be placed inside the exterior pocket 204. Once the ozone generator 200 is in place, the fastening mechanism 208 may be fastened to secure the ozone generator 200 within the exterior pocket 204. With the conduit second end 234 positioned midway between the flexible bag's first and second ends 102, 104 a user may position the partition intermediate the conduit second end 234 and the flexible bag's first end 102. The user may then place the ozone destruction catalyst 300 into the mesh interior pocket 112.

Use of the Ozone Removal Assembly

In various embodiments, after the odor removal assembly 10 has been assembled it is ready for use. In using the odor removal assembly 10, a user may place one or more items such as an athletic jersey, athletic shoes, hunting gear, and/or other sporting gear or other items into the interior of the bag's central housing 105 through the flexible bag's opening 115. These items may be items that the user wishes to deodorize. In various embodiments, the user may place items with similar levels of odor into the flexible bag 100 at the same time. For instance, if the user has socks and shoes from a short walk as well as hunting apparel from a long weekend hunt that needs to be deodorized, the user may desire to deodorize these items separately as the hunting gear may require a longer deodorizing session to be fully deodorized. Once the items have been placed into the flexible bag 100, the user may close the flexible bag's opening 115 by moving the fastening mechanism 120 from the open orientation to the closed orientation.

In some embodiments, the user may then lock the fastening mechanism 120 using a suitable locking mechanism as described above. When the fastening mechanism 120 is in the locked orientation, the user may plug the ozone generator' power cord 218 into a suitable power source (e.g., a wall plug or a car plug) and then turn the ozone generator 200 on using the power button 228. A user may select the level of ozone to be expelled from the ozone generator 200 by pressing either the up button 224 or the down button 226 depending upon the length of the time and level of ozone required to deodorize the items placed into the flexible bag 100. For example, for particularly foul odors, the user may elect to have the ozone generator 200 generate ozone for 30 minutes. For mild odors, the user may, for example, elect to have the ozone generator 200 generate ozone for a shorter period of time, such as five minutes.

In using some embodiments of the odor removal assembly 10, if the assembly's ozone sensor senses that the level of ozone within the bag exceeds a pre-determined threshold, the ozone generator's controller will turn off the ozone generator 200 so that ozone is no longer expelled from the ozone generator 200. Similarly, if the bag opening sensor senses that the bag has been opened, the automatic shutoff system will turn off the ozone generator 200 so that ozone is no longer expelled from the ozone generator 200.

Exemplary Use

Sports Equipment

In a particular example of a user using the odor removal assembly 10, a user desiring to deodorize sports equipment such as shoes, socks, shorts, and a shirt from a long run may set up the odor removal assembly 10 in the user's garage by plugging the ozone generator's power cord 218 into a wall outlet located in the user's garage. After placing the sports equipment into the flexible bag 100 and closing the bag 100, the user may consult the ozone generator user interface 214 regarding the correct length of time to set the timer 230 for. Because the user is desiring to kill any bacteria that may be on the sports equipment, the user may turn the ozone generator 200 on and press the up button 224 once to set the ozone generator 200 to a "kill bacteria" setting. This, may, for example, turn the ozone generator 200 on for 10 minutes, which may be a suitable amount of time for killing bacteria on items.

Once the full 10-minute cycle has been completed, the user may leave the sports equipment in the flexible bag 100 with the fastening mechanism 120 (e.g., a zipper) closed to allow the ozone destruction catalyst 300 to catalyze the remaining ozone in the bag 100. The user may then remove the sports equipment from the bag and test the odor of the sports equipment by smelling it. If the sports equipment requires further deodorizing, the user may place the sports equipment back into the bag 100 and repeat the steps listed above. If the user determines that undesired odor is still prevalent in the sports equipment, the user may, for example, increase the level of ozone produced by the ozone generator 200 from 10 minutes to 15 minutes.

This process may be repeated as many times as is necessary to remove undesired odors from the sports equipment. However, if the ozone sensor determines that the level of ozone outside the bag (e.g., within the garage, which may be closed) exceeds a pre-determined threshold, the assembly's controller may turn off the ozone generator 200 to prevent the ozone generator 200 from expelling any more ozone. Once the ozone sensor determines that the level of ozone outside the bag is less than a pre-determined threshold value, the controller may again allow the user to turn on the ozone generator 200 to run a deodorizing session.

In certain embodiments, a user may wish to use the assembly away from their home. It should be understood that, in various embodiments, the portable nature of the assembly may allow the assembly to be used away from a user's home (e.g., within a user's car, in the clubhouse of a golf course, or any other suitable location). This may be advantageous in that it may allow a user to deodorize sporting equipment or other items in essentially any suitable location. In particular embodiments, the assembly may include a battery pack that is used to supply power to the ozone generator 200, which may enhance the portable nature of the assembly.

CONCLUSION

Many modifications and other embodiments of the invention will come to mind to one skilled in the art to which this invention pertains, having the benefit of the teaching presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for the purposes of limitation.

I claim:

1. An assembly for removing odors from clothing or other items, the assembly comprising:
    a flexible bag defining an interior and a selectively closeable opening that is dimensioned so that: (A) when the opening is in an open orientation, a user may place clothing, or one or more other objects, into the interior of the bag through the opening; and (B) when the opening is in a closed orientation, a user is prevented from placing clothing or one or more other objects into the interior of the bag through the opening, the bag comprising;
    at least one partition within the interior of the bag that is adapted to be moved between: (1) a first position in which the at least one partition cooperates with one or more interior walls of the bag to form a first interior chamber of a first size adjacent a first particular side of the partition and a second interior chamber of a first size adjacent a second particular side of the partition; and (2) a second position in which the at least one partition cooperates with the one or more interior walls of the bag to form a first interior chamber of a second size adjacent the first particular side of the partition and a second interior chamber of a second size adjacent the second particular side of the partition;
    a fastening mechanism for selectively maintaining the bag in the closed orientation;
    an exterior pocket formed on an exterior of the flexible bag, wherein the exterior pocket is configured to receive an ozone generator;
    an opening formed in a common wall between the exterior pocket and the interior of the flexible bag;
    an ozone generator that is adapted to generate ozone gas and to expel the ozone gas from the ozone generator through an outlet; and
    at least one conduit having a first end coupled to the outlet of the ozone generator and a second end, wherein:
        the at least one conduit passes through the opening from the exterior pocket into the interior of the flexible bag; and
        the at least one conduit second end comprises a single opening and is secured to a surface of the interior of the flexible bag;
    wherein
        when the at least one partition is in the first position, the at least one conduit is in direct gaseous communication with the first interior chamber of the first size and not in direct gaseous communication with the second interior chamber of the first size; and
        when the at least one partition is in the second position, the at least one conduit is in direct gaseous communication with the second interior chamber of the second size and not in direct gaseous communication with the first interior chamber of the second size.

2. The assembly of claim 1, wherein the assembly further comprises an ozone destruction catalyst support assembly that is adapted for supporting the ozone destruction catalyst within the interior of the flexible bag.

3. The assembly of claim 2, wherein the ozone destruction catalyst support assembly comprises at least one mesh pocket.

4. The assembly of claim 1, wherein:
    the ozone generator is received in the exterior pocket and adjacent an outer portion of the flexible bag; and
    an outlet of the tubing is adjacent a central portion of the interior of the flexible bag.

5. The assembly of claim 1, wherein the assembly comprises an automatic shutoff system that is adapted to prevent the operation of the ozone generator at least partially in response to one or more pre-determined conditions being satisfied.

6. The assembly of claim 5, wherein the one or more pre-determined conditions comprise a pre-determined ozone level being exceeded outside of the flexible bag.

7. The assembly of claim 5, wherein the one or more pre-determined conditions comprise a pre-determined ozone level being exceeded within the interior of the flexible bag.

8. The assembly of claim 5, wherein the one or more pre-determined conditions comprise the opening being in the open orientation.

9. The assembly of claim 1, wherein the flexible bag is made of fabric.

10. The assembly of claim 1, wherein the flexible bag is dimensioned to hold athletic apparel.

11. The assembly of claim 1, wherein the flexible bag comprises a central housing that is at least partially coated with an ozone destruction material.

12. The assembly of claim 1, wherein the first interior chamber of the first size is larger than the second interior chamber of the first size.

* * * * *